United States Patent US 9,347,909 B2
Su  May 24, 2016

(54) SAMPLE-RETAINABLE BIOSENSOR TEST STRIP

(71) Applicant: Rapha Bio Ltd., New Taipei (TW)

(72) Inventor: Chin-Hui Su, New Taipei (TW)

(73) Assignee: Rapha Bio Ltd., New Taipei (TW)

( * ) Notice: Subject to any disclaimer, the term of this patent is extended or adjusted under 35 U.S.C. 154(b) by 234 days.

(21) Appl. No.: 14/269,945

(22) Filed: May 5, 2014

(65) Prior Publication Data

US 2014/0332377 A1    Nov. 13, 2014

(30) Foreign Application Priority Data

May 10, 2013    (TW) .................................. 102208770

(51) Int. Cl.
*G01N 27/327* (2006.01)

(52) U.S. Cl.
CPC .................................. *G01N 27/327* (2013.01)

(58) Field of Classification Search
CPC .................................................... G01N 27/327
See application file for complete search history.

(56) References Cited

U.S. PATENT DOCUMENTS

2012/0037513 A1\* 2/2012 Lindemann ................ 205/777.5
2015/0176143 A1\* 6/2015 Samproni ................... 205/777.5

\* cited by examiner

*Primary Examiner* — Jennifer Dieterle
(74) *Attorney, Agent, or Firm* — Wang Law Firm, Inc.

(57) ABSTRACT

A biosensor test strip includes: a first working electrode and a second working electrode formed on a base plate, having the second working electrode circumferentially surrounding the first working electrode to define a reaction pool within the second working electrode having a biological reagent provided in the reaction pool. Upon feeding a liquid sample of a user or patient into the reaction pool, the liquid sample will be well retained in the reaction pool to be reacted with the reagent to produce a signal which is then converted to be a readable data as displayed on a measurement apparatus or meter.

16 Claims, 14 Drawing Sheets

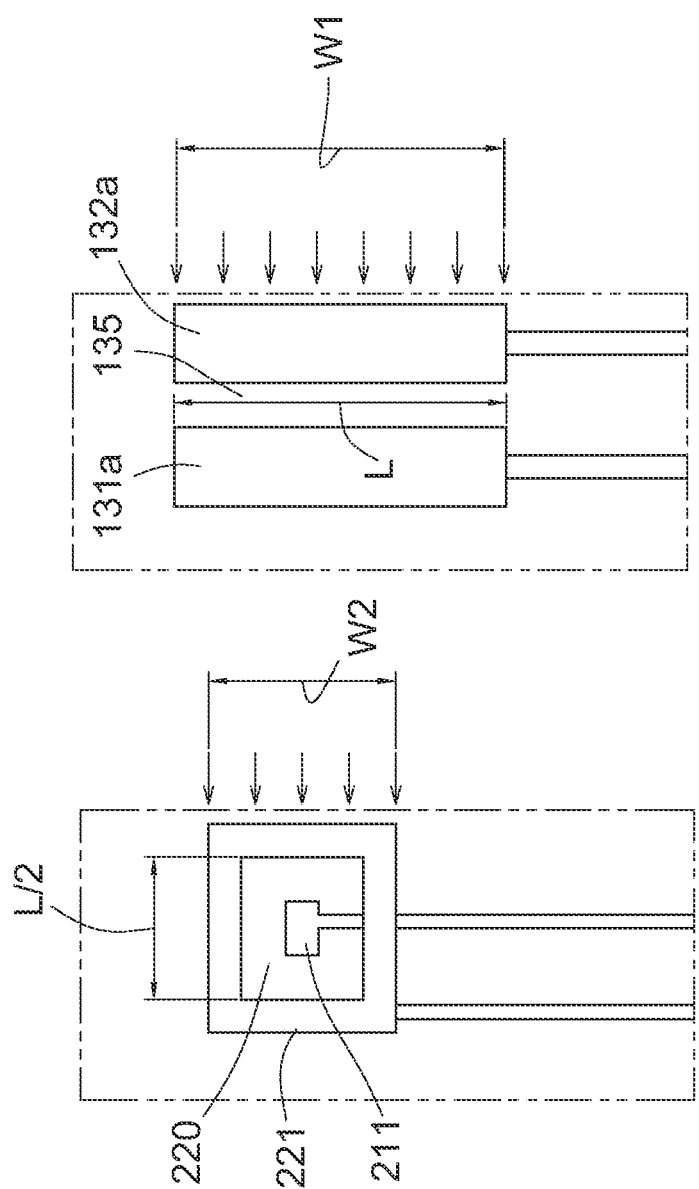

SAMPLE-RETAINABLE BIOSENSOR TEST STRIP

RELATED APPLICATION

This application claims the benefit of a Taiwanese patent application, 102208770, filed on May 10, 2013, the specification of which is incorporated here by this reference.

BACKGROUND OF THE INVENTION

A conventional biosensor test strip 10 as shown in FIGS. 1 and 2 comprises: a cover plate 11, a spacer plate 12 and a base plate 13 combinably superimposed to form the test strip 10. The base plate 13 is printed thereon with a first electrode 131, a second electrode 132, a conducting electrode 133, and a reference electrode 134. A first working electrode 131*a* is formed on a terminal portion of the first electrode 131; while a second working electrode 132*a* is formed on a terminal portion of the second electrode 132. A reaction zone 135 is defined between the first working electrode 131*a* and the second working electrode 132*a*, having a biological reagent 136 (such as an enzyme) is provided in the reaction zone 135. Upon feeding a user's liquid sample into the reaction zone 135, the sample will be reacted with the reagent 136 electrochemically to produce an impedance signal across the first and second electrodes 131, 132 to be converted into a readable data (such as a concentration of blood glucose, blood lipid, etc.) to be displayed on a measurement apparatus or meter. Such an impedance signal from the first and second electrodes 131, 132 may be commensurate with the reference electrode 134.

However, such a conventional test strip 10 has the following drawbacks:
1. The reaction zone 135 is an open area without being confined or limited by any wall, thereby easily spreading or losing the liquid sample nearby to cause measurement errors and affect measurement precision.
2. Larger quantity of the user's liquid sample is required in order to provide or compensate sample enough to be efficiently sensed in the "open" reaction zone 135. This may scare the user or patient, making him or her uncomfortable by sucking much blood as required.
3. Whenever feeding the liquid sample into the reaction zone 135, the sample must be penetrated capillary through an aperture between the cover plate 11 and the electrode 132*a* to "reach" the reaction zone 135 finally. However, there is no means for limiting or guiding the liquid sample to be smoothly penetrated into the reaction zone (i.e., the slim area between the two electrodes 132*a*, 131*a*). The liquid sample may be spread sidewardly capillary, with only a partial "stream" flowing into the reaction zone. So, it requires further means or method to ensure (double-check) the liquid sample to be safely led into the reaction zone, causing measurement inconvenience or wasting related resources.

Another prior art of U.S. Pat. No. 6,939,450 disclosed a biosensor including a device having a flow channel (114) into which a liquid sample is drawn therein and flows therethrough by means of capillary attraction.

However, such a device still has the following drawbacks:
1. Once the liquid sample is introduced into the sensor area and reaction site, the liquid sample may flow capillary through the flow channel (114) lengthwise, or may spread sidewardly, without being stably retained within the reaction site to be reacted with the reagent, thereby easily causing examination error and affecting test precision.
2. Larger quantity of liquid sample, such as a patient's blood, is required (even unwelcome) in order to compensate the capillary or spreading loss when introduced onto the test strip.
3. A flow-terminating interface (118*a*), such as openings (122*a*), should be provided to form a barrier to disrupt the force of capillary attraction that causes the liquid to flow in the flow channel. Such a flow-terminating interface may increase the production complexity and cost of the biosensor strip, and may also deteriorate the product quality since the plural openings (122*a*) may weaken the product strength.

The present inventor has found the drawbacks of the prior arts, and invented the present sample-retainable biosensor test strip.

SUMMARY OF THE INVENTION

The object of the present invention is to provide a biosensor test strip including: a first working electrode and a second working electrode formed on a base plate, having the second working electrode circumferentially surrounding the first working electrode to define a reaction pool within the second working electrode having a biological reagent provided in the reaction pool, whereby upon feeding a liquid sample of a user or patient into the reaction pool, the liquid sample will be well retained in the reaction pool to be reacted with the reagent to produce a signal which is then converted to be a readable date as displayed on a measurement apparatus or meter, to render a comfortable and reliable measurement with high precision.

BRIEF DESCRIPTION OF THE DRAWINGS

FIG. 17 is an illustration showing the feeding of liquid sample into the conventional strip of FIG. 1;

FIG. 18 shows the feeding of liquid sample into the reaction pool of the present invention;

DETAILED DESCRIPTION

As shown in FIGS. 3-6, the biosensor test strip 20 of the present invention may be inserted into a measurement (or detection) apparatus or meter 30 which comprises a slot 31 for inserting the test strip 20 therein, and means for analyzing the liquid sample as filled in the test strip, and converting the corresponding signal of test result to be readable data as shown on display 32 for the user or medical personnels. The test strip 20 of the present invention may be used for examining the concentration in a human blood, such as: glucose, cholesterol, triglyceride, uric acid, HbAlc, lead ion, cadmium ion, mercury ion, copper ion, etc.

Figure 3:
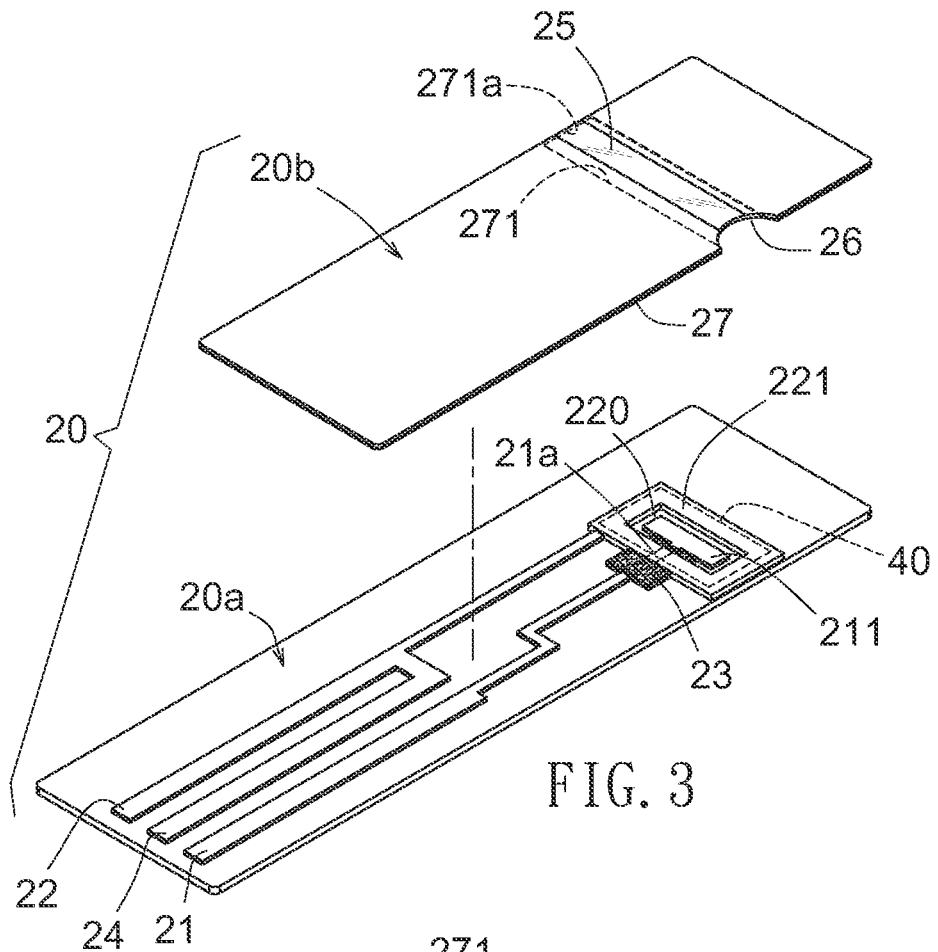
FIG. 3 is an exploded view of the test strip of the present invention.
Figure 4:
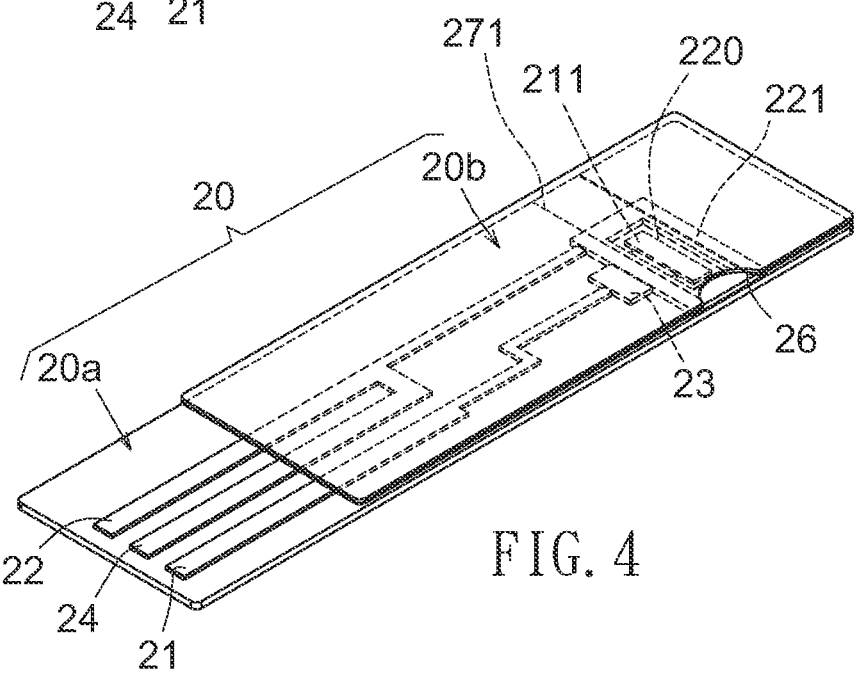
FIG. 4 is an illustration of the present invention as assembled from FIG. 3.
Figure 5:
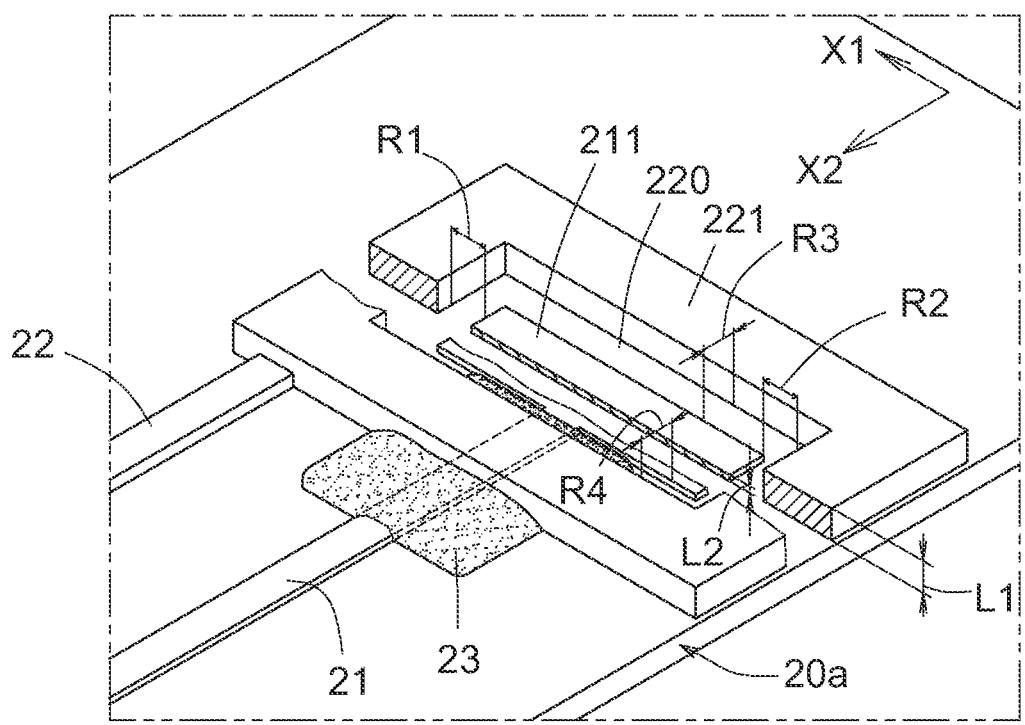
FIG. 5 is a partial illustration of the present invention as enlarged from FIG. 3.

As shown in FIGS. 3, 4 and 5, the biosensor test strip 20 of the present invention comprises: a base plate 20a, and a cover plate 20b.

The base plate 20a comprises: a first electrode 21 electrically connected with a first working electrode 211; a second electrode 22 electrically connected with a second working electrode 221. The second working electrode 221 is formed as a closed loop to circumferentially surround the first working electrode 211 within the loop of the second working electrode 221 and to define a reaction pool 220 as confined within the loop. A biochemical reagent 40 is deposited, attached or provided in such a reaction pool 220 to be in contact with the first and second working electrodes 211, 221 to be reacted with an examination or liquid sample as fed into the reaction pool 220 in order to obtain a measurement data of the sample as filled into the test strip 20 of the present invention; and an electrically insulating layer 23 disposed in between the second working electrode 221 and a terminal portion 21a, which is formed on an end portion of the first electrode 21 to be connected with the first working electrode 211 and is underlaid the second working electrode 221 as dotted line shown in FIG. 3.

The loop of the second working electrode 221 may be formed as a rectangular shape, a circular shape, an elliptic shape, or any other shapes, not limited in the present invention.

As shown in FIG. 5, the reaction pool 220 is formed within the loop of the second working electrode 221 having a height of L1 above the top surface of the base plate 20a, with the loop of the second working electrode 221 (like a "wall") circumferentially confining the first working electrode 211 within the loop of the second working electrode 221. The height L1 of the second working electrode 221 is higher than a height L2 of the first working electrode 211 (above the top surface of the base plate 20a).

Therefore, the liquid sample as fed into the reaction pool 220 will be stably retained in the pool 220 as confined by the loop of the second working electrode 221 without outward leakage to reveal the advantages for the present invention as follows:

1. The liquid sample is well retained in the loop (reaction pool) without leakage to thereby reduce the quantity as supplied from the user. For instance, if for checking the concentration of a user's blood glucose, the blood as sucked from the user will be greatly reduced.
2. The sample as retained in the reaction pool 220 will render enough time and environment for performing complete electrochemical reaction between the liquid sample and the reagent 40 to obtain a reliable examination signal and minimize the examination error, thereby increasing the precision of the test result.

Figure 6:
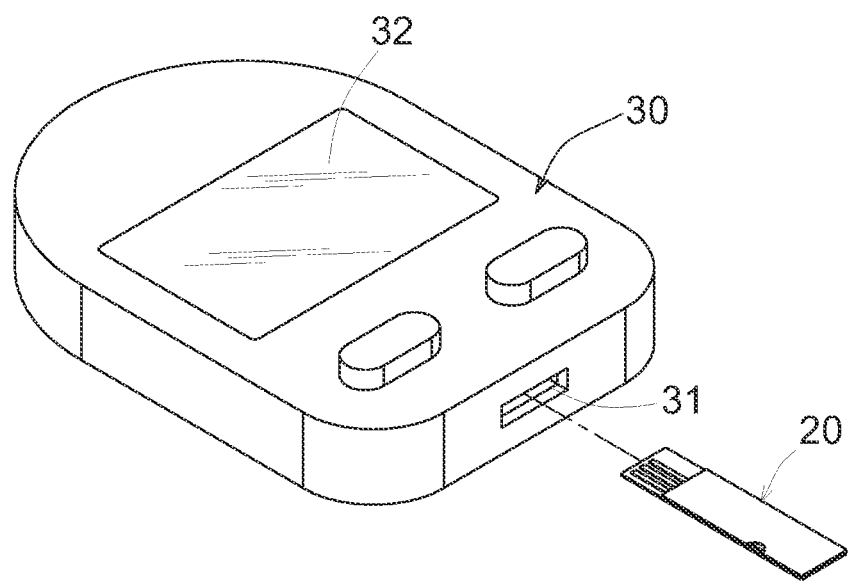
FIG. 6 shows a measurement operation in accordance with the present invention.

As shown in FIGS. 3 and 6, the test strip 20 further comprises a conducting electrode 24 electrically connected to the first electrode 21 or the second electrode 22, whereby upon the insertion of the test strip 20 into the measurement apparatus 30, the conducting electrode 24 will provide an impedance (circuit) signal to automatically start the measurement apparatus 30 and to identify the category of the test strip. The conducting electrode 24 may be juxtapositionally connected to either the first electrode 21 or the second electrode 22 as shown in FIG. 3.

The cover plate 20b may be treated to be hydrophilic. The cover plate 20b is formed with a feeding port 26 adjacent to the second working electrode 221 for filling liquid sample into the reaction pool 220 as capillary transferring between the cover plate 20b and the second working electrode 221. The cover plate 20b is superimposed and bonded on the base plate 20a by adhesive or tape.

The biochemical reagent 40 as used in the present invention may include an enzyme, antibody, antigen, microorganism cells, and animal or plant cells having biological identification ingredients, and a mixture solution of electrically conductive medium and buffer solution. The materials of the reagent 40 are not limited in this invention.

Whenever an electrochemical reaction is conducted between the liquid sample and the reagent 40 in the reaction pool 220, a reaction signal will be produced between the first electrodes 21 and second electrode 22. Such a reaction signal is transmitted to the measurement (or detection) apparatus 30 to be analyzed and compared to obtain a corresponding detection signal which is outputted and converted to be readable data as shown on the display 32 of the apparatus 30 to provide the necessary examination data for the user or patient.

As shown in FIG. 5, a longitudinal distance between the first working electrode 211 and the second working electrode 221 such as a first longitudinal distance R1 and a second longitudinal distance R2 may be defined along a longitudinal axis X1; while a latitudinal distance between the first and second working electrodes 211, 221 such as a first latitudinal distance R3 and a second latitudinal distance R4 may be defined along a latitudinal axis X2 (X1, X2 are merely defined for FIG. 5).

Even the above-mentioned longitudinal or latitudinal distance, R1-R4, may be varied during production, the total impedance, however, is kept uniform in the reaction pool in order to obtain a precise measurement data.

Figure 1:
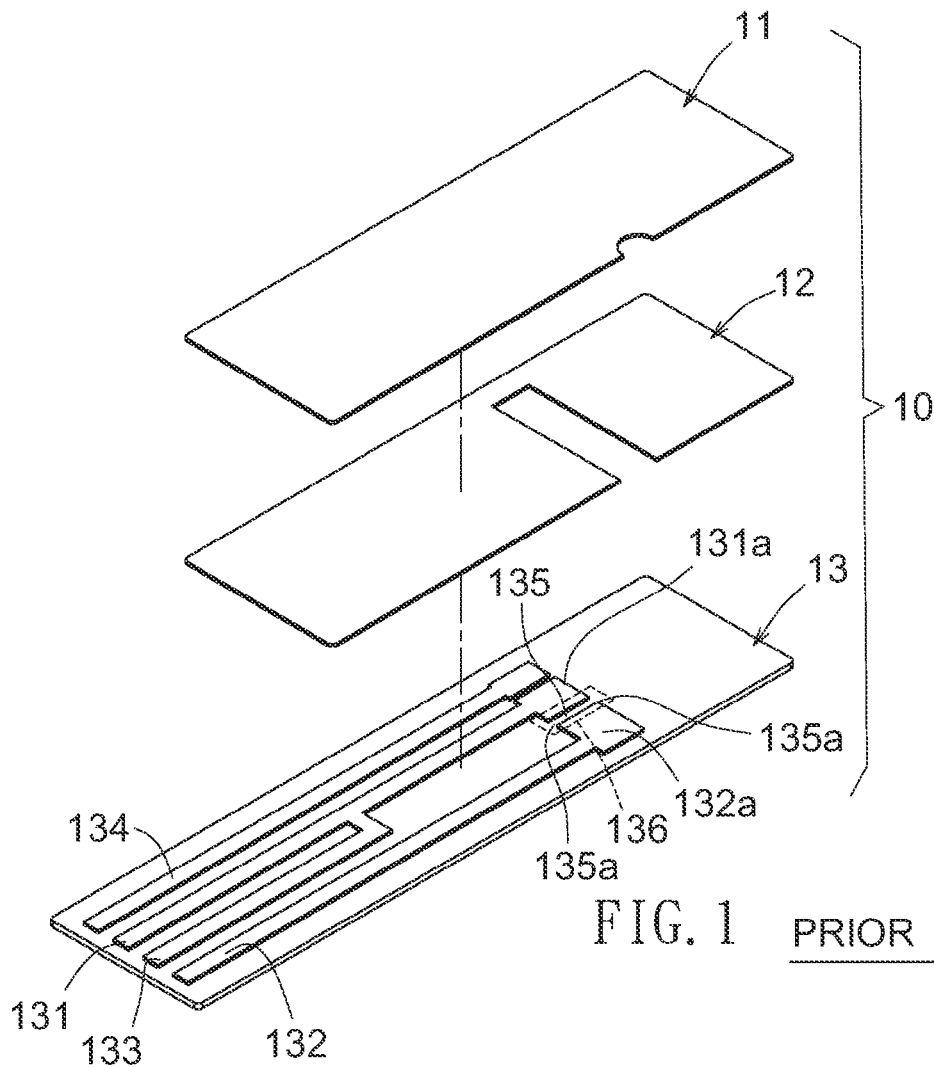
FIG. 1 is an exploded view of a conventional biosensor test strip.

During the production, even there may be slight variation of locations for printing the first and second working electrodes 211, 221 on the base plate 20a, the impedance in the reaction pool 220 is always equal to thereby obtain a reliable measurement result regardless of the small printing errors when produced batchwise. This may prevent from examination errors due to time lag when detecting and transferring the signals of a conventional test strip having varied distance between the first and second working electrodes (such as numerals 131a, 132a as shown in FIG. 1).

As shown in FIG. 3, the second working electrode 221, the insulating layer 23 and the terminal portion 21a of the first electrode 21 are superimposed on the top or upper surface of the base plate 20a to form a three-dimensional bridge-like structure, wherein the insulating layer 23 serves as an electrical insulator between the second working electrode 221 and the terminal portion 21a of the first electrode 21 to prevent short-circuit therebetween.

The first and second electrodes 21, 22 and the conducting electrode 24 may be made of graphite, platinum, sliver, aurum, and other metallic or non-metallic materials, but not limited in this invention.

The insulating layer 23 may be printed, adhered or coated in between the first electrode 21 and the second working electrode 221. The forming methods of the insulating layer 23 are not limited in the present invention.

When using the test strip 20 of the present invention for checking blood glucose, the first and second working electrodes 211, 221 may be made of same metallic materials or non-metallic materials such as graphite. When using the test strip of the present invention for checking blood lipid, one of the two working electrodes 211, 221 may be made of metallic materials, while the other may be made of non-metallic materials. According to the experiments, the metallic material is preferably selected from silver, and the non-metallic material may be graphite preferably.

Figure 2:
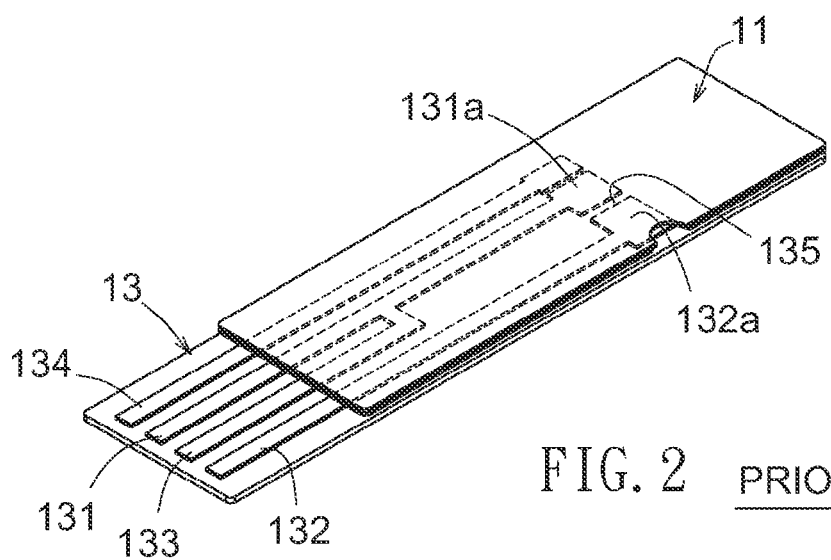
FIG. 2 is an illustration showing a test strip as assembled from FIG. 1.

As shown in FIG. 17 (which is an illustration based upon the prior art as shown in FIG. 1), a reaction zone (or area) 135 is defined between the first working electrode 131a and second working electrode 132a having a longer length L of the reaction zone 135, and a wider width W1 of port for inputting (dropping) the liquid sample into the test strip, thereby requiring a larger quantity of the liquid sample (as taken from the user's blood) for feeding the samples into the test strip for penetrating the liquid sample into the reaction zone 135 and thereby requiring a longer reaction and detection time for checking the liquid sample by using the conventional test strip as shown in FIGS. 1, 2 and 17.

Comparatively, as shown in FIGS. 3, 4 and 18 of the present invention, a reaction pool 220 is defined between the first working electrode 211 and the second working electrode 221 having a shorter length ½L of the reaction pool and narrower width W2 of port for feeding liquid sample thereinto, thereby requiring a shorter reaction and detection time as well as little sample quantity for checking the liquid sample than the conventional test strip (as shown in FIGS. 1 and 17), and thereby being superior to the prior art.

The cover plate 20b of the present invention may be made of plastic sheet having a transparent window 25 formed on the sheet and positioned above the reaction pool 220 for visual observation of the penetration or reaction status of the liquid sample as fed into the reaction pool 220. An input (or feeding) port 26 is formed on an edge portion of the transparent window 25 for feeding or inputting the liquid sample into the reaction pool 220.

As shown in FIG. 3, the cover plate 20b includes an adhesive layer 27 formed on a bottom surface (FIG. 14) of the cover plate 20b to be bonded with the base plate 20a. A non-adhesive passage 271 is transversely formed across the bottom surface of the cover plate 20b and positioned above the second working electrode 221 to release air outwardly in the pool 220 or in between the cover plate 20b and the electrodes 221, 211. A side opening 271a is formed on an exit of the passage 271 opposite to the input port 26 to be communicated externally to release or vent air outwardly to thereby smoothly feed the liquid sample into the reaction pool 220. The adhesive layer 27 should be electrically insulative. Other means for venting air may be further designed.

The test strip 20 is made with the following steps:
1. The base plate 20a is fixed on a processing machine;
2. Pattern printing is applied to print the first electrode 21, the first working electrode 211, the second electrode 22 and conducting electrode 24 on the base plate 20a;
3. Applying the insulating layer 23 on the first electrode 21;
4. Forming the second working electrode 221 on the second electrode 22 on the base plate 20a, electrically connecting the second working electrode 221 with the second electrode 22; and superimposing the second working electrode 221 on the insulating layer 23 which is superimposed on the terminal portion 21a of the first electrode 21;
5. Putting the biological reagent 40 into the reaction pool 220 to be in contact with the second working electrode 221 and the first working electrode 211;
6. Drying the reagent 40 at low temperature to cure or harden the reagent;
7. Binding the cover plate 20b on the base plate 20a; and
8. Cutting or finishing the test strip to form a final product.

Figure 7:
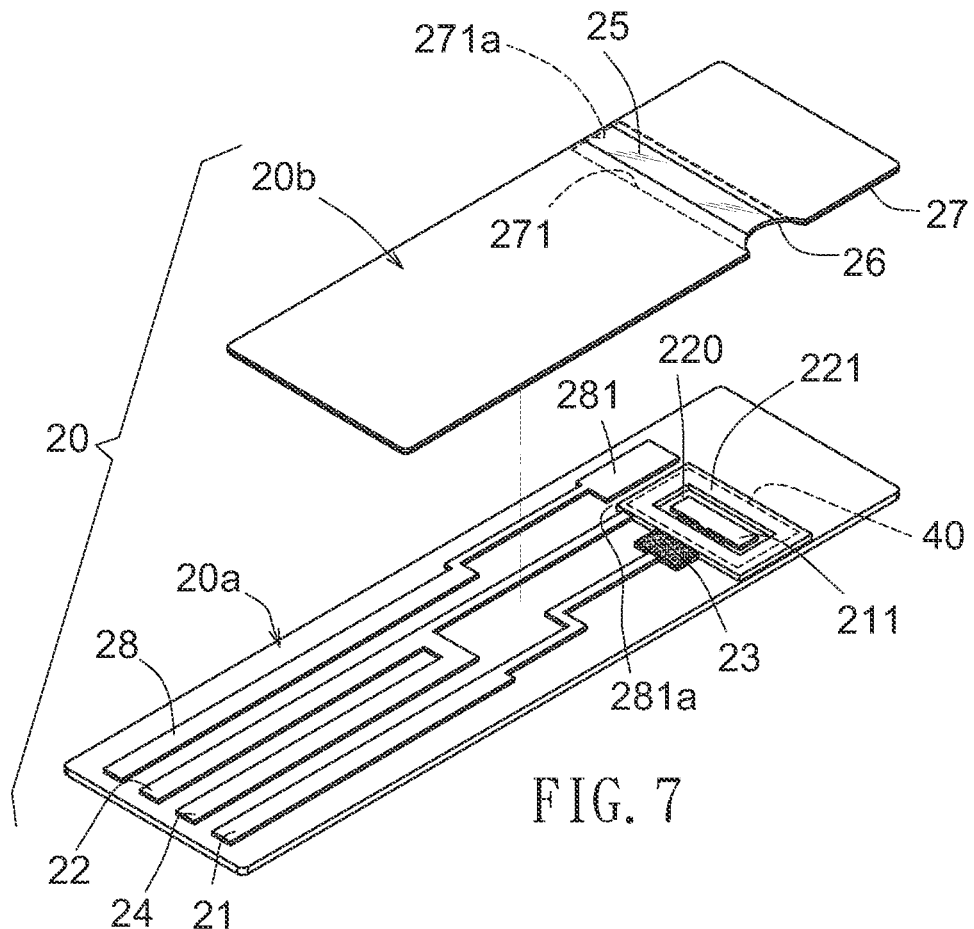
FIG. 7 is an exploded view of a second preferred embodiment of the present invention.
Figure 8:
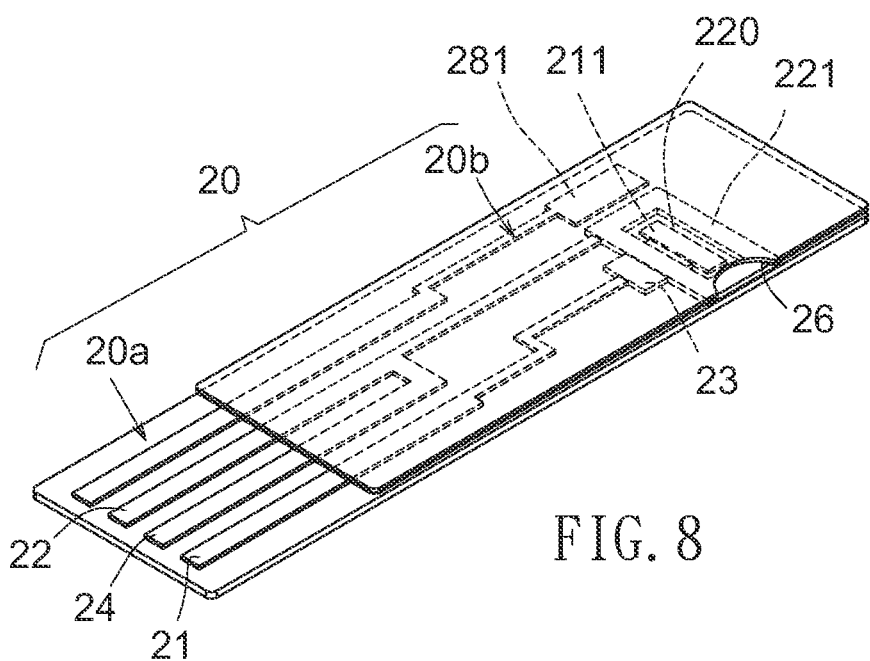
FIG. 8 is an illustration of the present invention when assembled from FIG. 7.

As shown in FIGS. 7 and 8, the test strip of the present invention further comprises a reference electrode 28, which is electrically connected with (and which may be integrally formed with) a reference working electrode 281, formed on the base plate 20a. The reference working electrode 281 is approaching the reaction pool 220 with an aperture 281a defined between the second working electrode 221 and the reference working electrode 281.

Upon overflow of the liquid sample from the reaction pool 220 over the second working electrode 221, a signal will be triggered, when electrically connected with the reference working electrode 281, from the reference electrode 28 to serve for the following functions:
1. It will check whether the quantity of liquid sample is enough or not? Only enough quantity of liquid sample may overflow to trigger the signal.
2. There may be different time lags of signals as produced from the reaction pool 220 to the reference electrode 28 for different liquid samples. So, each time lag may serve as a parameter to be corresponding to a specific liquid sample having specific flow velocity, thereby helping identification of each liquid sample.
3. A data base may be set up in a measurement apparatus (or meter) for storing signal data of different liquid samples, which may serve for checking, calibration, or comparison for each test or analysis, thereby increasing the measurement precision or enhancing better medical management.

Figure 9:
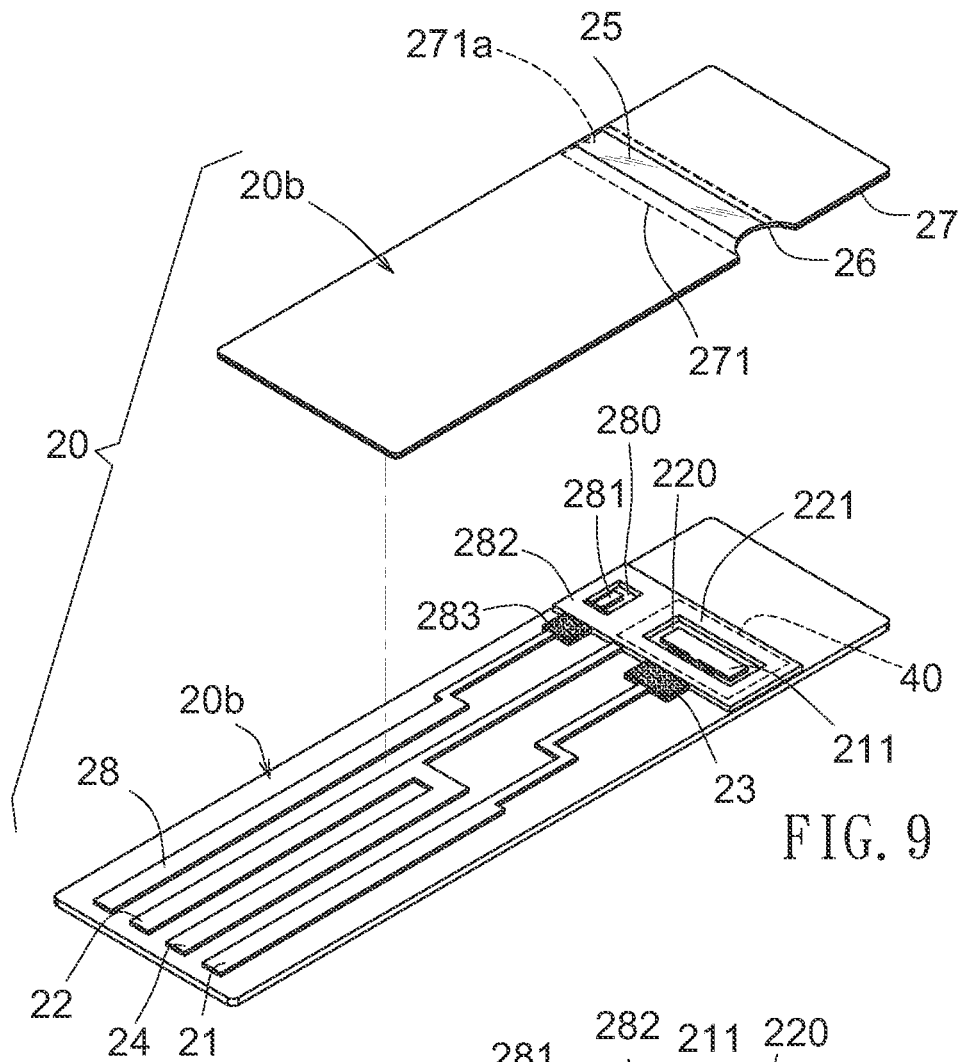
FIG. 9 shows a third embodiment of the present invention.
Figure 10:
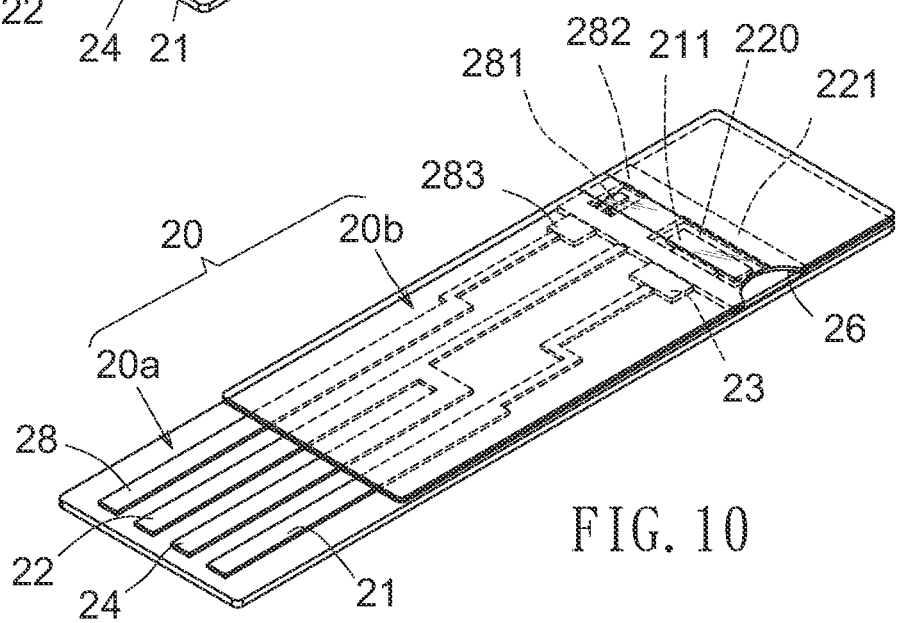
FIG. 10 is an illustration when assembled from FIG. 9.

As shown in FIGS. 9 and 10, a ring-shaped electrode 282, as electrically connected with the second electrode 22, is provided to be circumferentially disposed around the reference working electrode 281 to define an auxiliary reaction pool 280 between the ring-shaped electrode 282 and the reference working electrode 281, having an insulating layer 283 inserted between the ring-shaped electrode 282 and the reference electrode 28, whereby when a liquid sample is fed into the auxiliary reaction pool 280 to electrically connect the second electrode 22 and the reference electrode 28, an auxiliary signal will be triggered and outputted. Such an auxiliary signal may be provided for checking the flow velocity of liquid sample, quantity analysis of blood, rendering signals or data for calibration and comparison as performed in a measurement apparatus (or meter). The passage 271 allows the flow of liquid sample from the reaction pool 220 to the auxiliary pool 280.

The height of the ring-shaped electrode 282 should be higher than that of the reference working electrode 281 to form the auxiliary reaction pool 280 as a closed pool for well storing the liquid sample therein.

The ring-shaped electrode 282 may be integrally formed with the second working electrode 221. The ring-shaped electrode 282 and the second working electrode 221 may be made of the same materials. The reference working electrode 281 and the first working electrode 211 may be made of the same material. When the present invention is used for checking blood glucose, the ring-shaped electrode 282, the second working electrode 221, the reference working electrode 281 and the first working electrode 211 may be made of the same materials, for instance, made of the same metallic materials, or made of the same non-metallic materials. When used for checking blood lipid, the ring-shaped electrode 282 and the second working electrode 221 may be made of the same non-metallic materials, and the reference working electrode 281 and the first working electrode 211 may be made of the same metallic materials. Or, the ring-shaped electrode 282 and the second working electrode 221 may be made of the same metallic materials, while the reference working electrode 281 and the first working electrode 211 may be made of the same non-metallic materials when the present invention is served for checking blood lipid.

Figure 11:
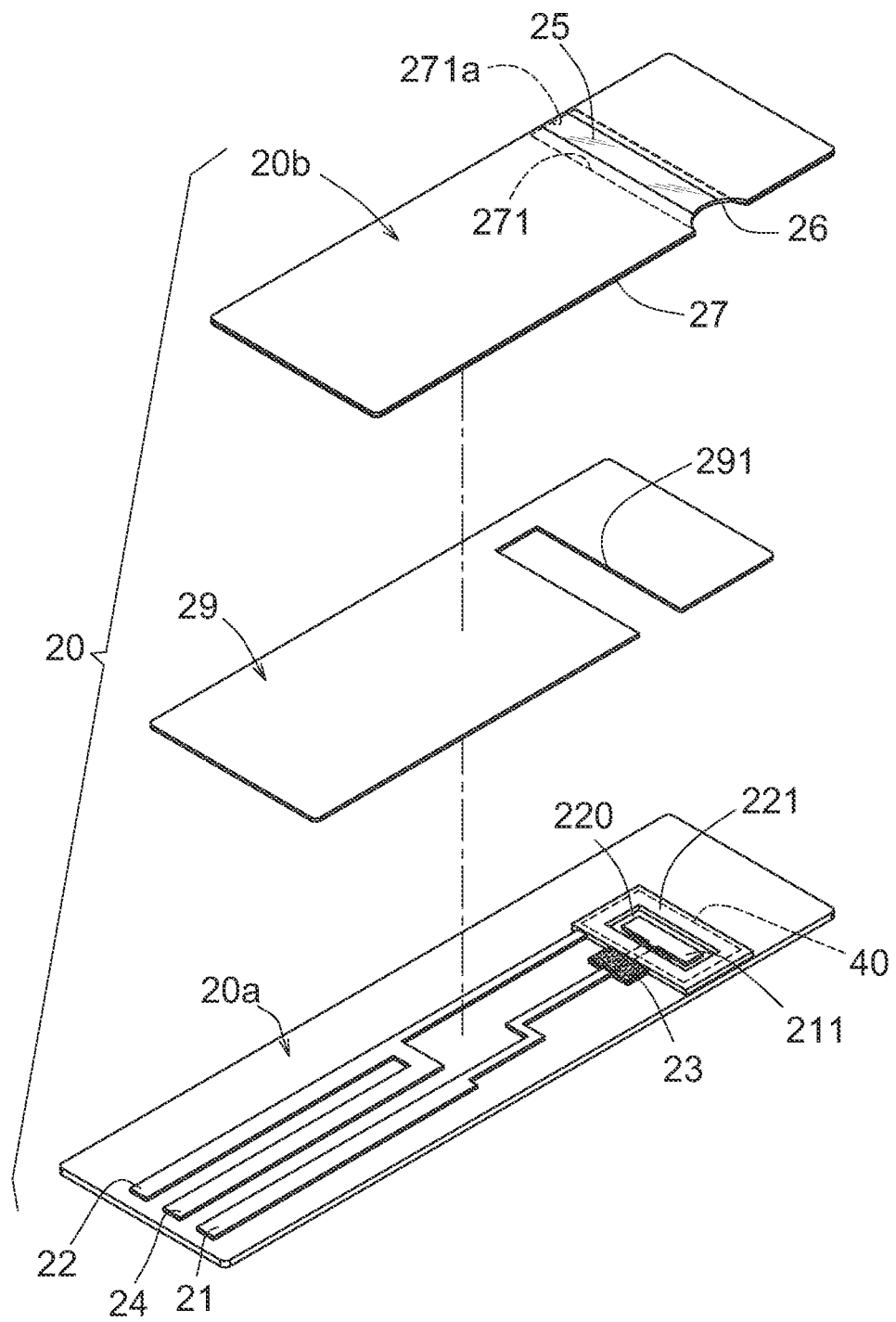
FIG. 11 is a perspective view of a fourth embodiment of the present invention.
Figure 12:
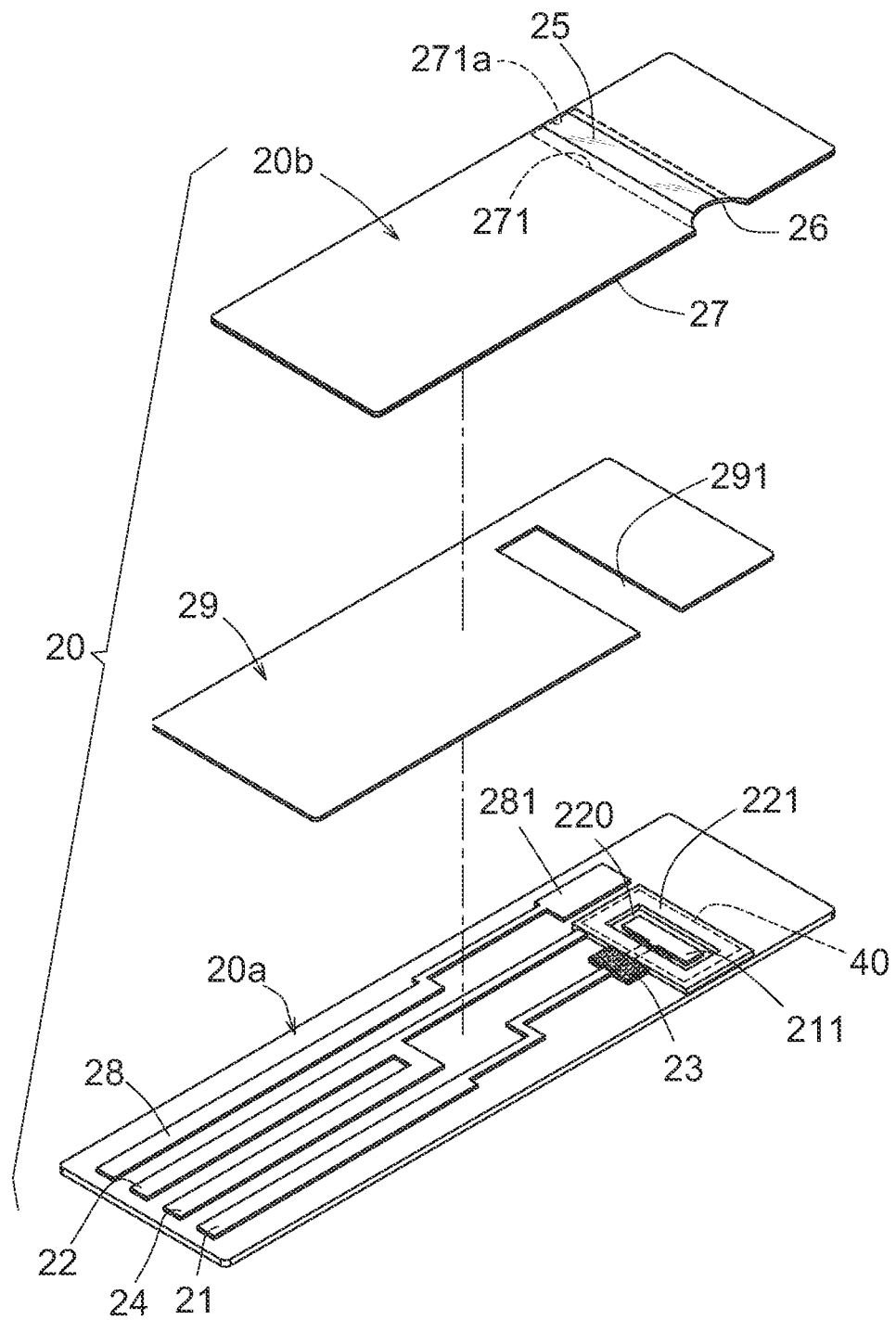
FIG. 12 shows a fifth embodiment of the present invention.
Figure 13:
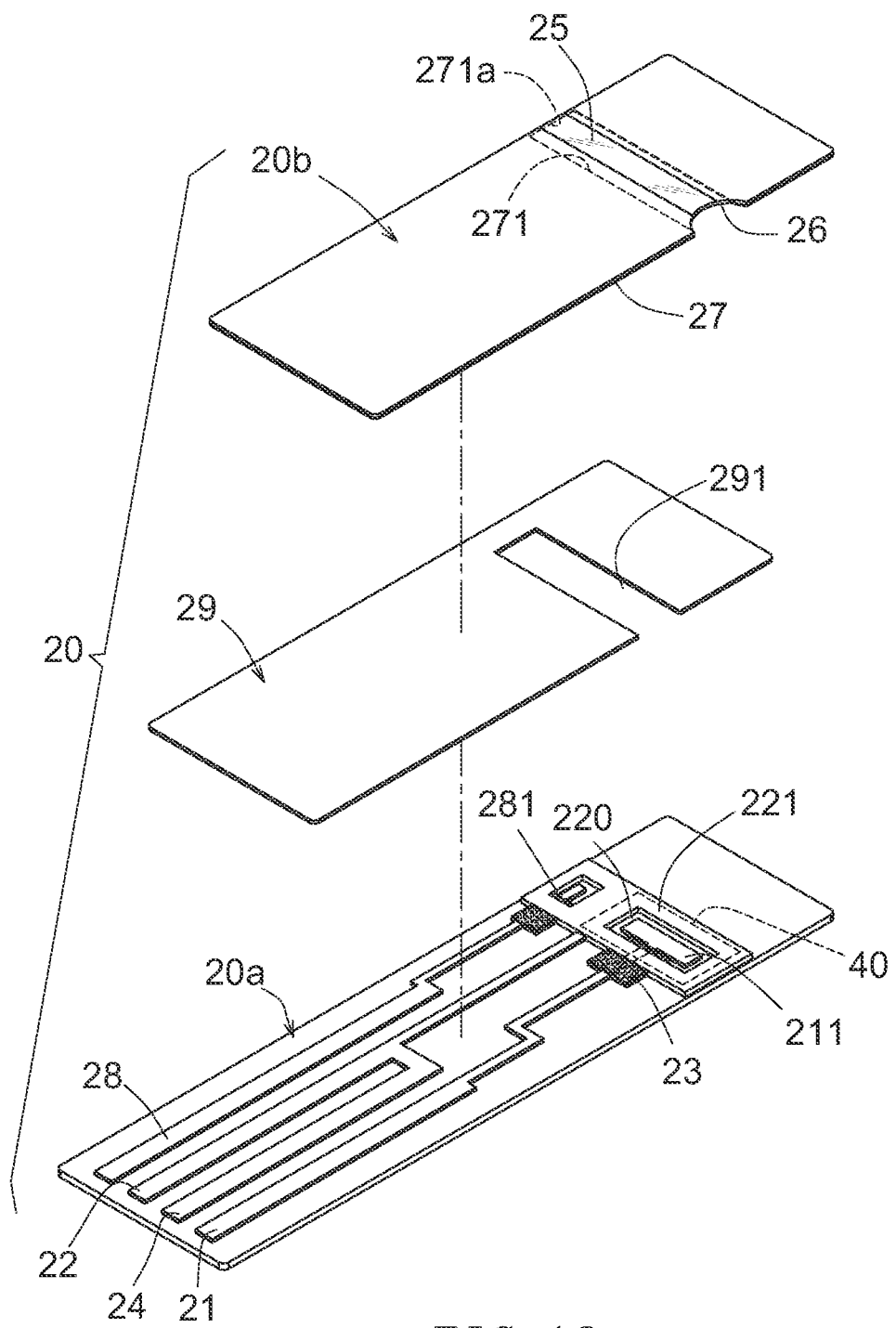
FIG. 13 shows a sixth embodiment of the present invention.

As shown in FIGS. 11, 12 and 13, a spacer plate 29 may be adhered in between the second working electrode 221 and the cover plate 20b, having a notch 291 transversely cut in the spacer plate 29 for providing a passage for liquid sample in the reaction pool 220. The notch 291 is projectively "superimposed" on or positioned above reaction pool 220. The spacer plate 29 may be made of polyethylene, polyvinyl chloride or other suitable polymers, but not limited in the present invention. The notch 291 of the spacer plate is projectively corresponding to and fluidically communicated with the passage 271 of the cover plate.

Figure 14:
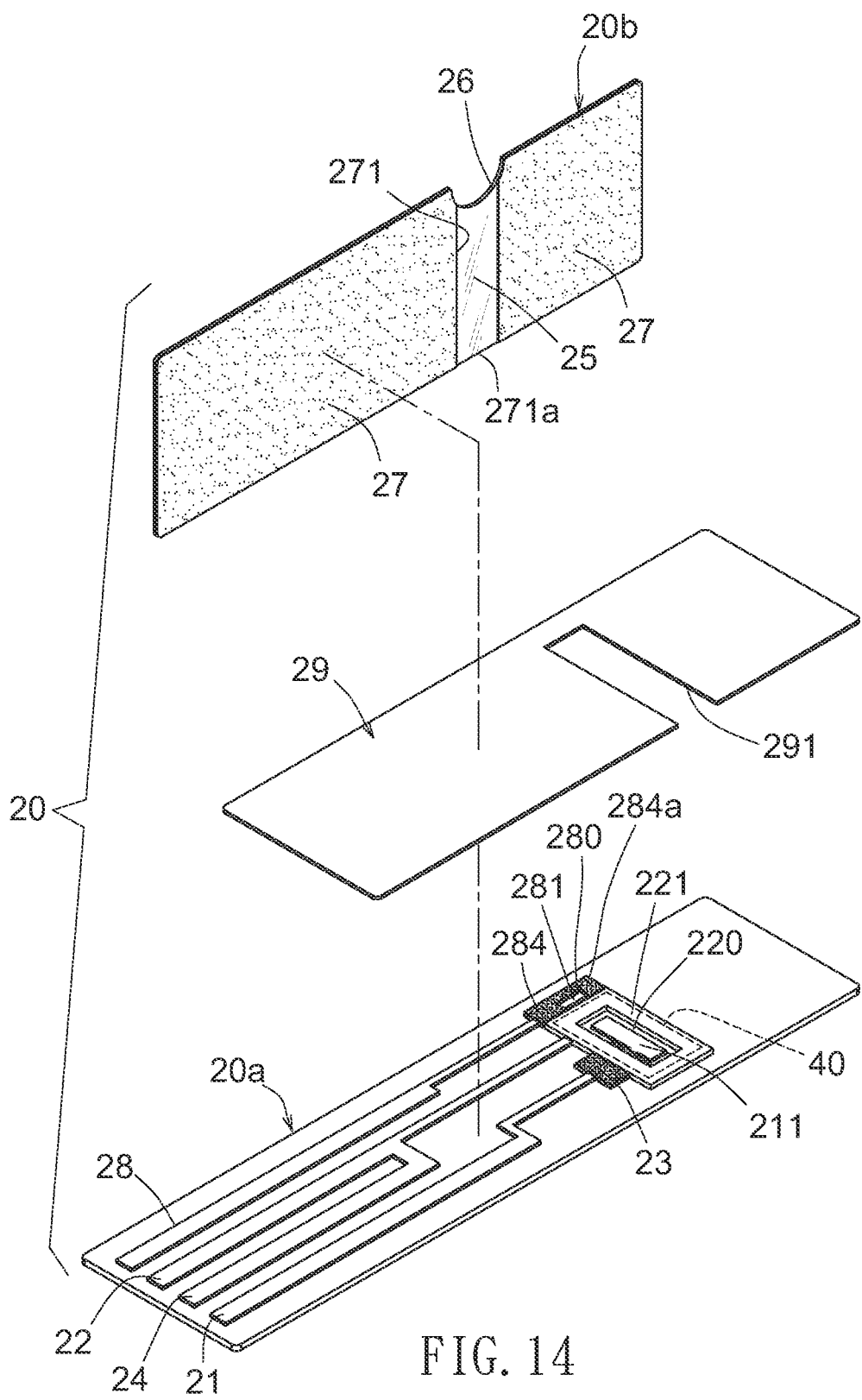
FIG. 14 shows a seventh embodiment of the present invention.
Figure 15:
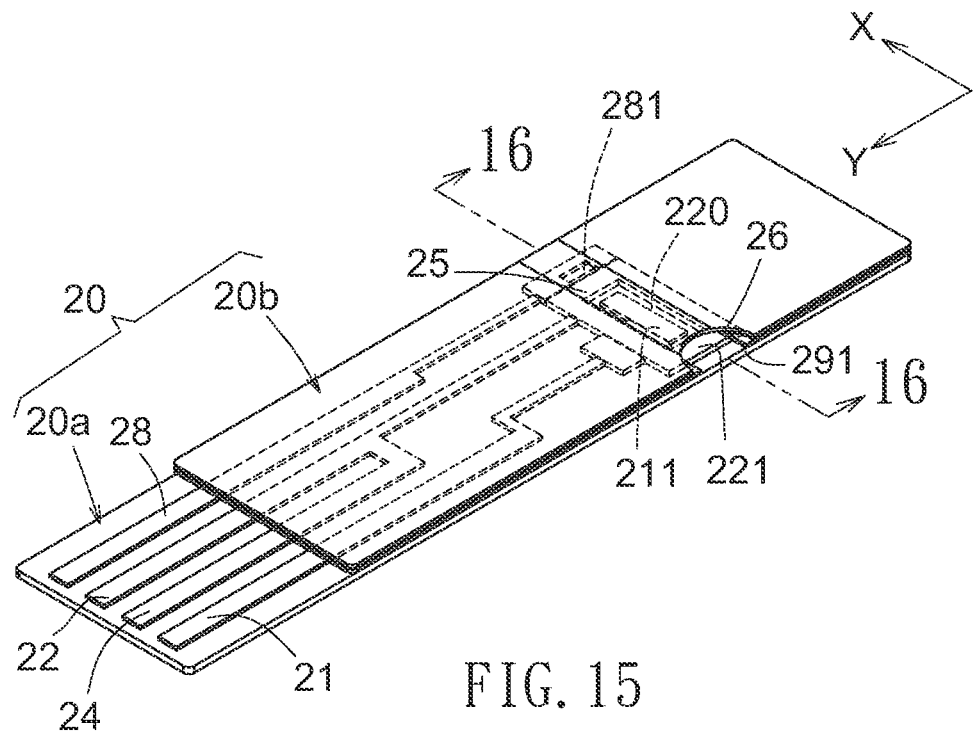
FIG. 15 shows a strip as assembled from FIG. 14.
Figure 16:
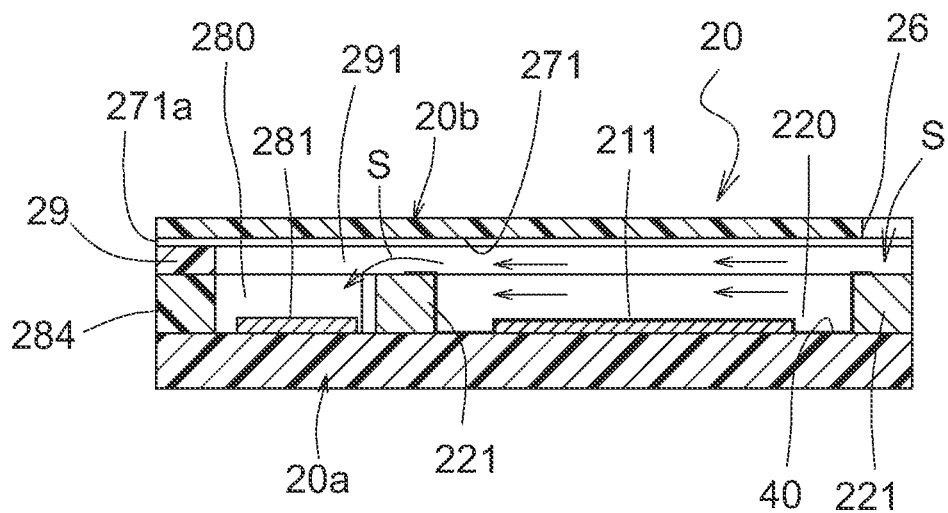
FIG. 16 is a cross-sectioned drawing as viewed from Line 16-16 direction of FIG. 15.

As shown in FIGS. 14, 15 and 16, the cover plate 20b, the spacer plate 29, and the base plate 20a (having electrodes 221, 211, 281 formed thereon) are superimposed together to input the liquid sample S into the reaction pool 220 as fed through the input (or feeding) port 26, as fluidically communicated with the passage 271 and the notch 291 and having air released through the side opening 271a, especially as shown in FIG. 16. The reference working electrode 281 is circumferentially surrounded with a U-shaped wall 284 to define an auxiliary reaction pool 280 (as modified from that of FIG. 9). The U-shaped wall 284 includes an access port 284a adjacent to and fluidically communicated with the reaction pool 220 through the passage 271 when the liquid sample S overflows the second working electrode 221 especially as shown in FIGS. 16 and 14. The liquid sample as entered into the auxiliary reaction pool 280 will trigger a signal which may serve to check whether the liquid sample quantity is enough or not, to thereby collect the information of flow velocity of different samples for better reading or calibration of the measured results for enhancing the precision of the measurement.

The U-shaped wall 284 may be made of electrically insulative materials, and may be coated, adhered, or printed on the base plate 20a and on the reference electrode 28. The top or upper surface of the U-shaped wall 284 is coplanar to the upper or top surface of the second working electrode 221 (FIG. 16) to be stably covered by the cover plate 20b as partitioned by the spacer plate 29.

As shown in FIG. 15 and the foregoing FIGS. 10 and 8, the input or feeding port 26 is formed on a right-side portion of the test strip to allow the liquid sample to flow into the reaction pool 220 transversely along an X-axis (FIG. 15). The X-axis is perpendicular to a Y-axis formed lengthwise on the test strip 20.

Figure 19:
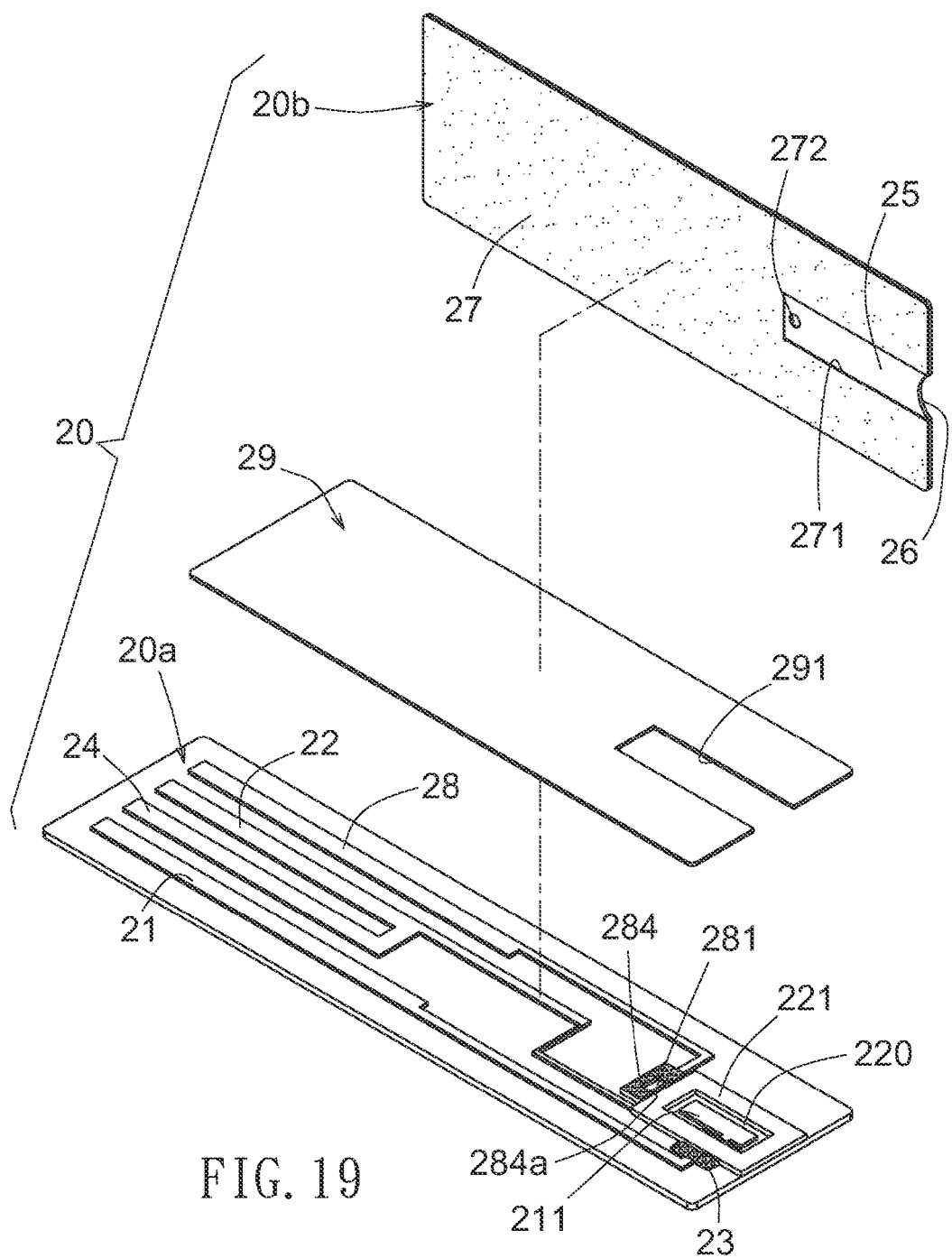
FIG. 19 is an exploded view of an eighth embodiment of the present invention.
Figure 20:
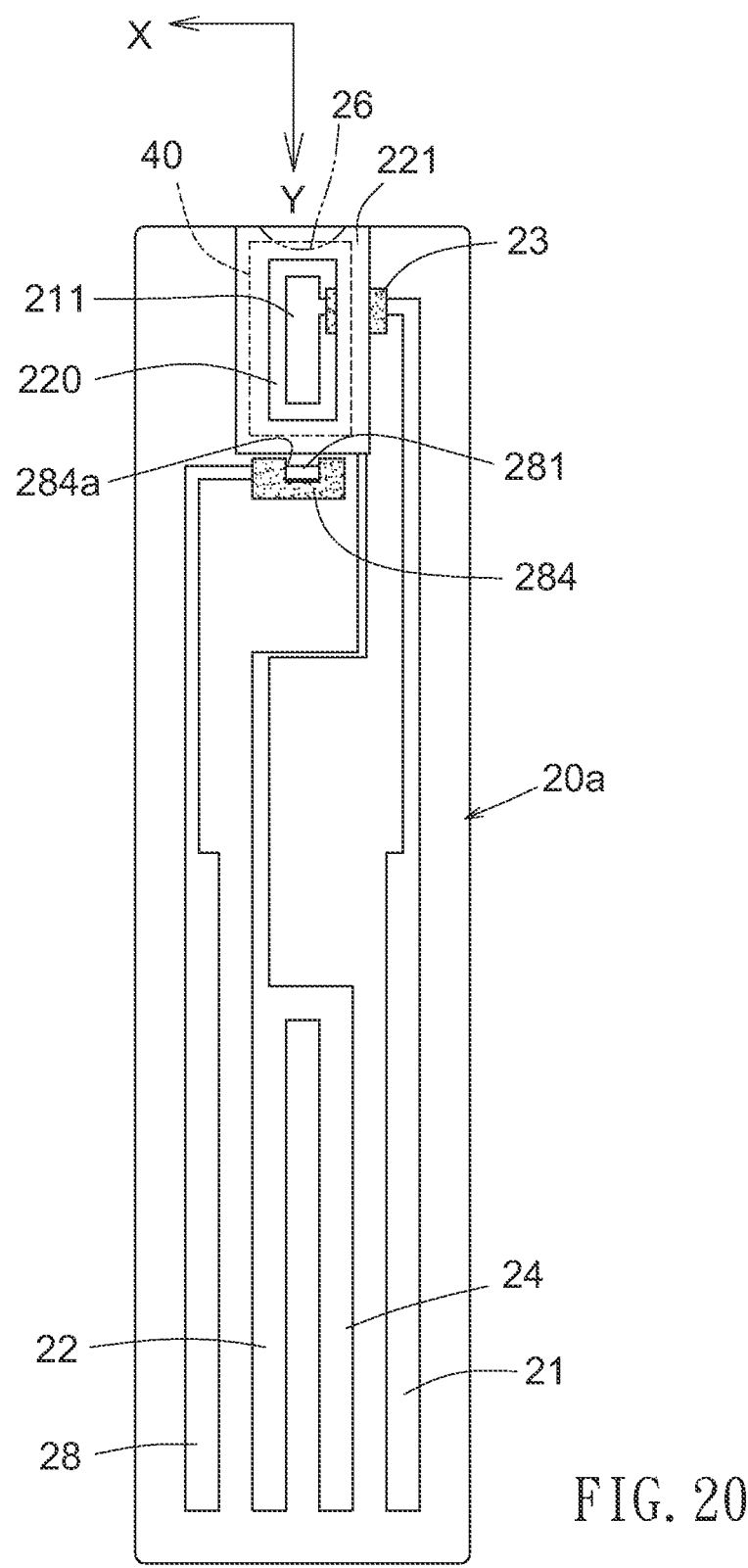
FIG. 20 is a plan view of the strip of FIG. 19.

As shown in FIGS. 19 and 20, the present invention is modified to form the inlet or feeding port 26 at an end (or front end) of the test strip 20 to feed the liquid sample from the port 26 to flow into the reaction pool 220 along the Y-axis formed lengthwise on the test strip 20. The passage 271, the spacer plate 29, the notch 291, the electrodes 211, 221, 281, and all the related elements may be correspondingly oriented lengthwise in a direction along the Y-axis as shown in FIGS. 19 and 20. An opening 272 is formed through the cover plate 20b for venting air. Such a Y-axis is perpendicular to the X-axis transversely formed on the test strip 20.

However, the locations, directions or arrangements of the feeding or inlet port 26 and the related electrodes or parts are not limited in the present invention.

The present invention is superior to the prior art or conventional test strips with the following advantages:

1. The second working electrode 221 circumferentially disposed around the first working electrode 211 will define a reaction pool 220 to retain the liquid sample well in the pool to enhance a complete electrochemical reaction between the reagent 40 and the liquid sample as performed in the pool, thereby increasing the measurement precision or reliability for testing the liquid sample.
2. The reaction pool 220 may greatly reduce the space or volume of the related electrodes or elements of the test strip, thereby decreasing the production cost and increasing the commercial value.
3. The liquid sample, as limited in the pool 220, will be required in a less quantity, which may comfort a patient without scaring big loss of his or her blood, and may also shorten the blood test time.
4. The user's or patient's blood sample is well retained or limited within the reaction pool 200 to prevent its outward spreading, thereby minimizing its possible contamination once his or her blood containing HIV or AIDS virus when disposing the test strip after test.

The present invention may be modified without departing from the spirit and scope of the present invention. The adhesive used in this invention should be electrically insulative if the adhesive may contact the related electrodes to make them short-circuited.

The invention claimed is:

1. A biosensor test strip comprising:
    a base plate;
    a first electrode electrically connected with a first working electrode formed on said base plate;
    a second electrode electrically connected with a second working electrode and formed on said base plate, said second working electrode formed as a closed loop and circumferentially surrounding said first working electrode to define a reaction pool within said closed loop of said second working electrode, having a biological reagent provided in said reaction pool to be in contact with said first working electrode and said second working electrode;
    an insulating layer inserted in between said first electrode and said second working electrode; and
    a cover plate superimposed on said base plate to cover all said electrodes and said base plate to form a biosensor test strip and having means formed in the test strip for venting air outwardly;
    whereby upon feeding of liquid sample as supplied from a user or patient into said reaction pool through a feeding port formed on an edge portion of said cover plate, said liquid sample will be reacted with said reagent to produce a signal, across said first and said second working electrodes within said reaction pool, and said signal will be converted to a readable data to be displayed on a measurement apparatus or meter.

2. A biosensor test strip according to claim 1, wherein said second working electrode has a height higher than a height of said first working electrode.

3. A test strip according to claim 1, wherein said base plate further includes a conducting electrode formed thereon to be electrically connected with either said first electrode or said second electrode.

4. A test strip according to claim 1, wherein said base plate further includes a reference electrode which is electrically connected with a reference working electrode, said reference working electrode approaching said reaction pool formed by said second working electrode.

5. A test strip according to claim 4, wherein said reference electrode is integrally formed with said reference working electrode.

6. A test strip according to claim 1, wherein said base plate further includes a reference electrode, which is electrically connected with a reference working electrode, said reference working electrode circumferentially surrounded by a ring-shaped electrode, said ring-shaped electrode electrically connected with said second electrode, having an auxiliary insulating layer inserted in between said ring-shaped electrode and said reference electrode.

7. A test strip according to claim 1, wherein said cover plate is formed with an adhesive layer on a bottom surface of said cover plate, said adhesive layer having a non-adhesive passage formed on the bottom surface of the cover plate, said passage projectively disposed above said second working electrode and fluidically communicated with said reaction pool when said cover plate is covered on said base plate; said passage communicated with said feeding port; and said cover having an opening formed in said passage opposite to said feeding port for venting air outwardly.

8. A test strip according to claim 1, wherein said cover plate includes a non-adhesive passage formed in a bottom surface of said cover plate and having an opening for venting air outwardly, and further includes a spacer plate adhered in between said cover plate and said second working electrode, having a notch cut in said spacer plate, said notch projectively corresponding to and fluidically communicated with said reaction pool as defined by surrounding said first working electrode within said second working electrode, and said notch projectively positioned to be corresponding to said passage of said cover plate and fluidically communicated with said passage.

9. A test strip according to claim 8, wherein said cover plate is treated to be hydrophilic, having a transparent window formed in said cover plate to be projectively positioned above said notch in said spacer plate, said window having a feeding port formed on an edge portion thereof.

10. A test strip according to claim 8, wherein said base plate further includes a reference electrode electrically connected with a reference working electrode on said base plate, said reference working electrode approaching said reaction pool as formed by said second working electrode, said reference working electrode projectively corresponding to said notch as cut in said spacer plate.

11. A test strip according to claim 10, wherein said reference working electrode is circumferentially surround by a U-shaped wall, having an access port formed in a side portion of said U-shaped wall and being facing and adjacent to said reaction pool of said second working electrode.

12. A test strip according to claim 11, wherein said U-shaped wall is made of electrically insulative materials, and having a top surface of said U-shaped wall coplanar to a top surface of said second working electrode.

13. A test strip according to claim 8, wherein said base plate further includes a conducting electrode electrically connected with either said first electrode or said second electrode formed on said base plate.

14. A test strip according to claim 8, wherein said second working electrode has a height higher than a height of said first working electrode.

15. A test strip according to claim 8, wherein said opening for venting air outwardly is formed in an exit of said passage transversely formed on the bottom surface of said cover plate, opposite to said feeding port formed in said cover plate.

16. A test strip according to claim 8, wherein said opening for venting air outwardly is formed through said cover plate and communicated with said passage.

* * * * *